United States Patent [19]

Jaffe

[11] 4,251,870
[45] Feb. 17, 1981

[54] CONTROL OF GASOLINE MANUFACTURE

[75] Inventor: Stephen B. Jaffe, Cherry Hill, N.J.

[73] Assignee: Mobil Oil Corporation, Fairfax, Va.

[21] Appl. No.: 117,377

[22] Filed: Jan. 31, 1980

Related U.S. Application Data

[63] Continuation of Ser. No. 754,678, Dec. 27, 1976, abandoned, which is a continuation-in-part of Ser. No. 610,591, Sep. 5, 1975, abandoned.

[51] Int. Cl.$^3$ .............................................. G06F 15/20
[52] U.S. Cl. .................... 364/500; 364/578; 364/118; 364/121; 73/23.1; 73/35
[58] Field of Search ............... 364/500, 578, 118, 121; 73/23.1, 35

[56] References Cited

U.S. PATENT DOCUMENTS

| | | | |
|---|---|---|---|
| 3,385,680 | 5/1968 | Feld et al. | 73/35 SR |
| 3,469,954 | 9/1969 | Hoffman | 73/35 |
| 3,501,700 | 3/1970 | Boyd, Jr. | 328/127 |
| 3,511,980 | 5/1970 | May | 364/499 |

Primary Examiner—Edward J. Wise
Attorney, Agent, or Firm—C. A. Huggett; M. G. Gilman

[57] ABSTRACT

A system for predicting the octane number of a substantially olefin-free gasoline or gasoline component. A sample of reformed gasoline is analyzed by means of a gas chromatograph in order to ascertain the presence and amount of its constituents. Signals representing both the identities of the various constituents and their percent volume are applied to a computer which includes means for associating the constituents with predetermined groups and combining the relative volumes of the constituents of each group. Subsequent apparatus assigns predetermined coefficients to each of the groups, after which the volumes of each group are multiplied by the group coefficient. The resulting products are then summed to produce a first expression A. A second expression B comprises the summed differences between the product of the volume and octane number, and the product of the volume, octane number and coefficient, for each group. The second expression is then combined according to the formulation $B/(1-A)$ to produce an estimation of the octane number of the sample. The octane number so derived is applied to control a process for the manufacture of gasoline or a gasoline component in modification of process conditions to achieve a result desired. The principles of the invention are applicable to the manufacture of gasoline and gasoline components generally.

3 Claims, 2 Drawing Figures

CONTROL OF GASOLINE MANUFACTURE

This is a continuation of application 754,678, filed Dec. 27, 1976 now abandoned.

BACKGROUND OF THE INVENTION

This application is a continuation-in-part of co-pending application Ser. No. 610,591 filed Sept. 5, 1975 abandoned. The present invention relates to means for deriving the octane number of a sample of gasoline and, more particularly, to improved means for calculating the octane number of a gasoline sample without resort to the traditional knock engine. The basic principles of deriving octane number for gasoline described hereinafter are applicable to generating signals for monitor and control of process units in which the gasoline output includes components additional to those here described.

Of the many chemical and physical characteristics of automotive gasoline one of the most important, and certainly the most broadly known, is octane rating. The octane rating, or octane number, is an arbitrary rating whereby the propensity for knocking or detonation of a given motor fuel is compared to that of "isooctane" (actually 2, 2, 4-trimethylpentane). The knock rating of isooctane has been arbitrarily assigned a value of 100; this figure is then used as a benchmark for comparing other motor fuels. Lesser octane numbers are derived from the percent of isooctane in a blend of isooctane and n-heptane which exhibits a knocking propensity equivalent to the fuel under test. While there are other characteristics or attributes of a motor fuel which are of great importance, the octane number is the most important single characteristic of the fuel and forms the basic consideration to be addressed when a motor fuel is to be blended from a plurality of different gasolines and/or additive compounds.

As is known to those skilled in the art, the propensity of an internal combustion engine to cause detonation or knocking is a function of many variables besides the fuel upon which it is operating. Compression ratio, combustion pressure, internal engine temperature, and combustion chamber configuration are but a few of the many considerations which affect the tendency of a given engine to knock. Therefore, in order to form a reliable basis for the comparison of different fuels the knock engines which are used for testing must conform as closely as possible to a common standard. Detailed standards have been adopted for the construction of knock engines and such engines have been widely manufactured for many years. Nonetheless, in order to assure tolerable accuracy of results the engines must be operated under closely guarded conditions, and the mechanical condition of the engines cannot be allowed to deteriorate. Even in view of the elaborate precautions taken in the manufacture and operation of knock engines, the repeatability (or degree of variation) of test results is not constant over a broad range of octane numbers but is best for fuels having octane ratings in the area of 90. The repeatability of knock engine measurements deteriorates as the measured octane numbers either ascend of descend from the range about 90.

Aside from the time and expense necessary to construct and maintain knock engines and efforts which have been made to automate their operation they are practically always manually operated, necessitating time-consuming trial and adjustment. Typically an engine is run until its temperature stabilizes, then the compression ratio is gradually increased by physically displacing the cylinder head of the engine downwardly towards the piston. In this manner, the internal pressure within the combustion chamber of the engine is gradually increased until the fuel being tested exhibits a knocking which is sensed by an appropriate transducer and displayed upon a meter. The meter is visually monitored by an operator who then, by a painstaking process of adjusting the engine, attempts to ascertain the true knock point of the fuel. Once the knock point is ascertained the octane rating of the fuel can be calculated by means of tables and correction factors.

The difficulties which inhere in the above-described procedure are apparent. While trained personnel using well-maintained equipment regularly achieve good results through the use of the knock engine test procedure, the procedure is time-consuming and not well adapted for deriving the octane ratings of a large number of samples in a relatively short time. The time-consuming nature of the knock engine test procedure also precludes closed-loop process control systems in refineries whereby an ongoing refining process may be continuously controlled in response to the perceived octane rating of the in-process fuel.

These drawbacks are also applicable to the blending of already-refined petroleum fractions. In order to compound a gasoline with a desired octane number, petroleum fractions of different octane numbers are sometimes blended together. While the octane number of each blending constituent may have been previously determined by means of a knock engine, the prediction of the octane rating of the blended fractions proceeds only upon estimates based on previous experience. One who wishes to blend certain petroleum fractions is then faced with the choice of either blending a small sample, subjecting it to a test on a knock engine, and if necessary, increasing or decreasing the proportions of ones of the constituents in a hit-or-miss fashion; or blending the entire amount required, based upon previous experience, and subsequently verifying the octane number of the resulting product through the use of the knock engine.

To date, experts in the field of petroleum processing have not been able to devise a generally applicable method for accurately predicting the octane number of a given blend of petroleum fractions. This is true even though the octane number of each constituent is known. The reason for this lies in the non-linear relationship which exists among the various constituents of the blend. For instance, if a first fraction having a known octane number of 90 is blended with an equal volume of another constituent, whose octane number is 80, a linear relationship would result in an octane number of 85 for the mixture. However, this is often not the case; and as more fractions are added to the blend, the unpredictability of the result increases.

For the foregoing reasons, many attempts have been made to develop a mathematical "model" or set of relationships which would allow a refiner to accurately predict the octane number of a given sample without resorting to the octane engine. To date, however, no such relationship has been found which extends over a substantial range of octane numbers, and which takes cognizance of all of the various constituents which may affect the octane rating of a gasoline. It will therefore be understood that it would be highly desirable to provide apparatus which will accurately predict the octane rating of the sample of a gasoline product.

It is thus an object of the present invention to provide means for calculating the octane number of the sample of a gasoline product.

It is another object of the invention to provide improved means for generating an estimate of the octane number of a given sample, which estimate falls substantially within the range of repeatability of a knock engine for similar octane numbers.

A further important object of the invention is the provision of a control technique by which a signal representing the octane number so derived is applied to control of a process unit from which the sample is derived.

SUMMARY OF THE INVENTION

Briefly stated, in accordance with one aspect of the invention the foregoing objects are achieved by providing a measuring apparatus which produces an output representative of the identity and the relative volume of each pure component of a sample of a gasoline product. The output of the measuring apparatus is then applied to a computer adapted to associate each of the components with one of several groups, and which additively combines the relative volumes of the pure components present in each of the groups. Octane number is then calculated by associating a pair of known terms with each group, one term representing the average octane number for the components of each group, and the other term being a number which is a function of the octane rating of the sample.

In a preferred embodiment, a signal is generated which is representative of the octane number so calculated and that signal is applied in a closed loop for control of the process unit from which the sample was taken.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawings in which:

DESCRIPTION OF A PREFERRED EMBODIMENT

Figure 1:
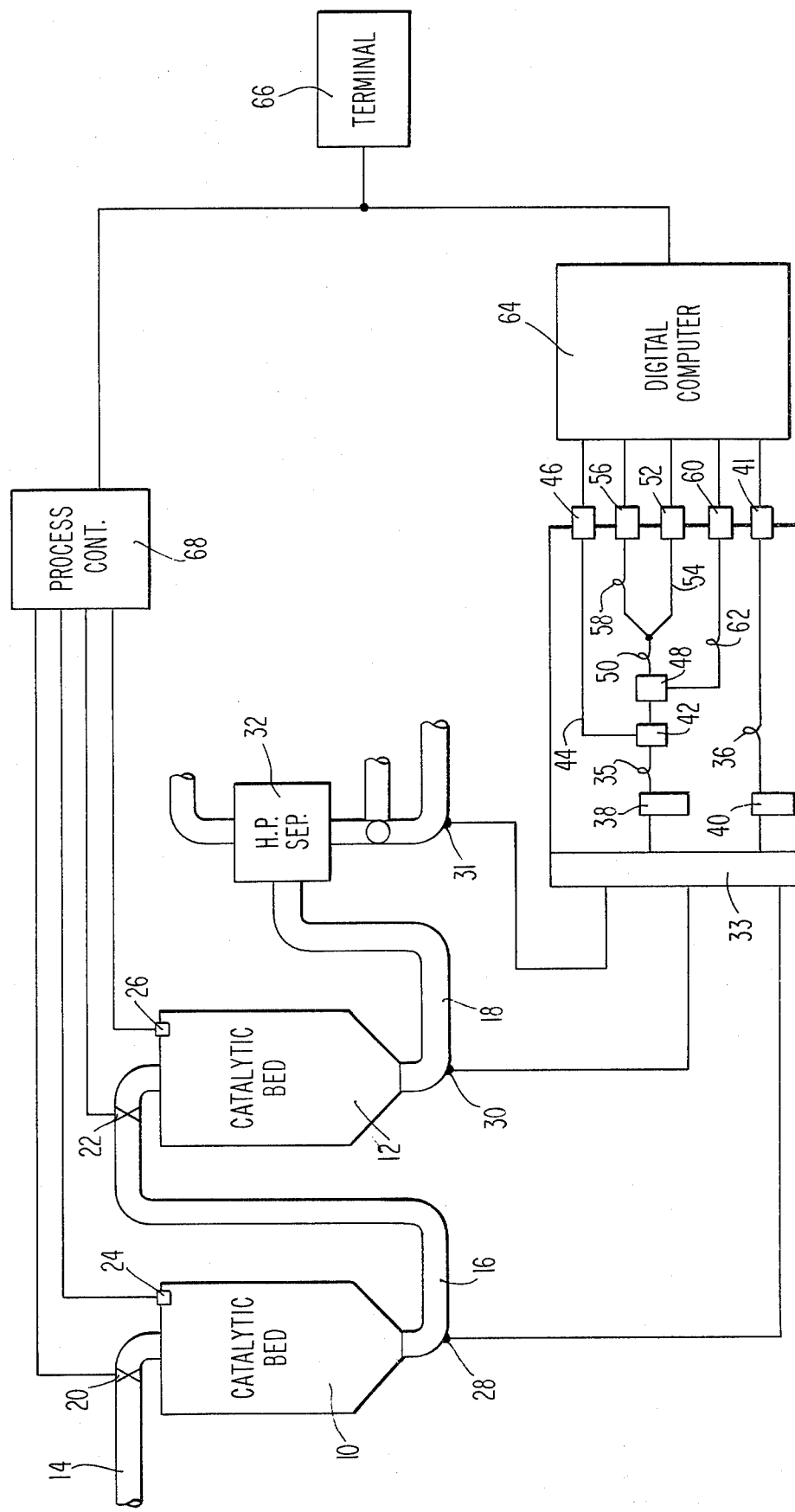
FIG. 1 is an idealized schematic diagram of a system for practicing the present invention.

In FIG. 1 there is shown in idealized, simplified form portions of a system for catalytically reforming a hydrocarbon stream in order to produce gasoline. It will be recognized that the reforming apparatus is depicted in generalized form, it being apparent to those skilled in the art that a number of catalytic reforming processes are fairly encompassed by the illustrated system.

A catalytic bed 10 is supplied with a hydrocarbon stream by means of input conduit 14. Intermediate conduit 16 passes the product of bed 10 to bed 12, the reformate produced thereby exiting by means of outlet conduit 18. In one satisfactorily tested embodiment, beds 10 and 12 comprise catalytic reformers of the fixed bed type although others may wish to use moving bed or fluidized bed apparatus. In addition, besides being applicable to conventional catalytic reforming processes the apparatus taught herein is equally useful for predicting octane numbers of the products of various proprietary reforming processes. Two of the latter processes, for example, are those designated M-forming and Selectoforming and which are proprietary to the Mobil Oil Corporation and its licensees.

As is known to those skilled in the art, reforming processes serve to produce an end product which differs somewhat from gasoline produced by cracking processes in that it is substantially free of olefins. The present invention is applicable to all reforming and similar processes, such processes being herein denominated converting processes.

As is customary with such systems the illustrated reforming apparatus is provided with various mechanisms for controlling flow rates, pressure, temperature, and other parameters which affect the ongoing process. In the illustrated apparatus valves 20 and 22 control the ingress of a hydrocarbon stream to catalytic beds 10 and 12 respectively. Heating units 24 and 26, also associated with catalytic beds 10 and 12 respectively, control the temperatures within the bed environment.

The schematic showing in FIG. 1 of a catalytic reformer with control loop operative to control inlet valves 20 and 22 and/or heaters 24 and 26 will be readily understood by those skilled in the art as means to modify two parameters of the process concerned with "severity" of reforming, namely space velocity and temperature. Other controls associated with other parameters are well known and aptly described in the literature.

The variables of Selectoforming and effect of variation therein are described in "Selectoforming—A Shape Selective Route to Higher Quality Gasoline and LPG", Burd and Maziuk, Proceedings, Division of Refining, American Petroleum Institute, 52, 190 (1972).

Near the exit of each bed 10 and 12 are placed taps 28 and 30 for deriving samples of the hydrocarbon stream in process. Another tap 31 is used to provide samples of the stream after reforming, and subsequent to the traversal by the stream of high pressure separator 32. The taps may be operated manually by means of suitable valving arrangements, or may alternatively be operated automatically to procure an appropriate sample at a predetermined time or in response to a sensed condition. The samples are applied by way of an appropriate manifold 33 to gas chromatograph 34 for identifying the various constituents of the sample, and determining their relative volumes.

While the techniques of gas chromatography are well known to those skilled in the art and it is contemplated that various chromatographic apparatus may be selected to suit a particular application, the chromatograph arrangement disclosed in FIG. 1 lends itself particularly well for use with the present system. In order to improve separation of the components of a sample, and thus the resolution thereof, the chromatograph includes a total of five columns. Two initial branches 35 and 36 are provided each of which has associated therewith a trap 38 and 40 respectively. Such traps are commercially available units, and commonly utilize liquid nitrogen for removing condensable waste fractions from the sample before introduction into a given column. Column 36 is particularly adapted to separate certain pure components of the sample, as indicated in Table I below and has a transducer 41 coupled to the discharge end thereof for producing an electrical signal reflecting the presence of a detected component.

As set forth in Table II below, chromatograph column 36 is responsive to particular ones of the components of the sample to be analyzed. Column 35, on the other hand, provides an initial partial separation of sample constituents preparatory to their introduction into a plurality of subsequent columns.

Column 35 terminates at valve 42, which passes the aromatics portion of the sample previously separated from the non-aromatic portion by column 35 to column 58 which is responsive to the aromatics components of the sample to be analyzed and then through a suitable conduit 44 to transducer 46. The position of valve 42 is changed at an appropriate time to pass the balance of the material flowing from column 35 to a second valve 48. In one position, valve 48 passes the received sample stream by way of column 50 to transducer 52 by means of an appropriate conduit 54. It will be understood that transducer 52 then produces indications of the presence of various components in the stream which are defined by the operation of column 50.

In its alternate orientation valve 48 passes another portion of the previously separated sample stream to transducer 60 through column 62. Column 62 serves to further separate and define predetermined components of the sample whose presence and relative volume are detected by transducer 60. In one embodiment the transducers coupled to the various columns may comprise dual flame ionization detectors model 009-0953/0954, manufactured by the Perkin-Elmer Corp.

Table I sets forth the operation of the various columns of chromatograph 34, indicating the specific components of a reformate sample which are intended to be defined by each column.

TABLE I

| Column | Sample Constituent |
|---|---|
| 58 | Aromatics |
| 50 | C1-C9 Paraffins and Napthanes |
| 62 | C10+ Paraffins and Naphthanes |
| 36 | C1-C3 Paraffins |
| 35 | Type separation of Aromatics from Non-Aromatics |

It will be understood that the transducer associated with any given column is adapted to produce signals indicating the presence of the constituents in that group of compounds identified with the respective column by Table I.

The transducer may also be responsive to other constituents of the partially separated sample stream, which arise at the transducer either before or after the constituents of interest for that particular unit. However, such spurious or duplicative signals can be easily avoided by scanning or interrogating the transducers only during appropriate time periods.

While the separation and identification of each component of a given sample could theoretically be achieved through the use of a single column, it has been found that the separation and identification process is enhanced by providing specialized columns adapted to separate only certain constituents, and providing means for applying the separated constituents to a particular transducer. In addition to achieving increased resolution, the illustrated system has the advantage of operating more rapidly than single column systems in that the separation and identification of at least some of the constituents may proceed simultaneously.

The signals from the various transducers are transferred to a digital computer 64 or similar device which operates upon the signals received from the transducers in a manner to be described. As is well known, a digital computer ordinarily comprises a complex, highly adaptable data computing and storage system. The system, or portions thereof, may be adapted (programmed) to serve as means for carrying out prescribed operations and manipulation of data. In the present system data derived from the signals is manipulated in a manner to be discussed subsequently in order to determine the octane number of the sample under test. The information thus derived may be subsequently passed to terminal 66 and/or applied to process controller 68.

By feeding back the signal to the process controller a closed loop system is constituted which varies process unit parameters in response to an analysis of a product sample. By this technique, deviation from a target octane number may be detected and appropriate remedial action taken for correction of the deviation in a matter of minutes. By contrast, prior practices involved transmission of a sample to the plant laboratory, analysis in due course and transmission of the octane number determination to a process unit operator who then decided on action to be taken. The expired hours in that control system can be such that need for correction is known only after the need has vanished. For example, a reformer charging 30,000 barrels of naphtha per day may have exhausted the charge stock in one supply tank and be operating on a different naphtha before it is known that the reforming operation was off target on stock from the now-exhausted tank. The present invention provides corrective action while the need therefor exists.

It has been found that a peculiar relationship exists which dictates an unexpected association of components with appropriate groups. The desired degree of accuracy, approximately that achieved by engine test of octane number, can be achieved if all the paraffins having eight or more carbon atoms, up to the maximum present in a gasoline or gasoline component (say 400° F. boiling point), are associated with two groups, namely straight chain (normal) compounds and those having branched chains (isocompounds). The paraffins of six or seven carbon atoms must be treated differently, if the desired degree of accuracy is to be achieved. The latter must be each broken into three groups for a total of six. In addition to the normal six carbon atom paraffin (n-hexane), there must be a group in which a single methyl group is in a side chain (monomethyl hexane) and a second group in which two methyl groups are in branched position. The latter dimethyl butanes are grouped as "doubly branched hexane". Similarly, the seven carbon compounds are associated with three groups: n-heptane, monomethyl heptane and doubly branched heptane. It will be immediately apparent that the last named group includes one compound in which the double branching arises from an ethyl group, namely 3-ethyl pentane.

This same peculiarity of grouping is used when the invention is applied to gasolines which contain in addition compounds not fitting any of the groups described herein. Such other compounds are grouped appropriately to their characteristics, but the paraffins of six, seven, or at least eight carbon atoms are grouped in the manner above specified.

Controller 68, which may, for example, be a Fisher model TL155 control station, is adapted to respond to signals indicative of the octane number of the reformate being sampled and operates to vary the settings of valves 20, 22 or temperature systems 24, 26 in accordance with a predetermined scheme to cause the octane number of the hydrocarbon stream to be maintained in a desired range.

Most prior attempts to predict the octane number of an analyzed sample have involved schemes for taking into account the amounts of various components present in the sample and somehow weighting each constituent in a manner which was thought to reflect its contribution to the octane rating of the total sample. In this vein many attempts have been made to establish a linear relationship which produced the desired result.

A linear relationship between octane number and the various components of a sample may be represented by the equation $$ON = \Sigma V_i B_i \tag{1}$$

where ON represents octane number of the sample, $V_i$ is the volume fraction of the ith component and $B_i$ is a coefficient for the ith component. On its face this approach seems eminently reasonable, particularly in view of the fact that an octane number represents the percent by volume of isooctane which is present in a particular mixture of isooctane and normal heptane. Isooctane (2, 2, 4 trimethylpentane) is arbitrarily assigned an octane number of 100, while normal heptane is assigned an octane number of 0. Therefore, a mixture of equal volumes of the two constituents will, by definition, produce a fuel having an octane number of 50.

However, the octane numbers of other mixtures of gasoline constituents do not vary in direct proportion to the volumes of the individual constituents. To date, no theory has been advanced which explains this effect for even two constituents; and when it is recognized that the total number of pure components in reformed gasoline is between 150 and 200 the complexity of the problem assumes proportions which have to date been dealt with successfully only on trial-and-error, empirical bases. This, despite continuing efforts to devise models which would successfully approximate the octane number of a given gasoline sample.

A number of kinetic models have been developed for use with petroleum refining processes. Some of these models are extremely useful and, for certain purposes, tolerably accurate. The models are used to predict the effect of various temperatures, pressures, flow rates, and other process variables on an in-process hydrocarbon stream. While such models find use in the controlling of on-going processes and in the analysis of new refining procedures, to date none have been developed which may be used to accurately estimate the octane number of a hydrocarbon stream over a substantial octane number range.

The apparatus which forms the subject matter of the present invention not only is capable of predicting octane numbers of a hydrocarbon sample but does so over a broader range of octane numbers than was heretofore possible, and moreover exhibits a repeatability of results which corresponds closely to the repeatability characteristics of the classical knock engine test procedure.

The mathematical relationships upon which the operation of the inventive apparatus is based will now be discussed, using appropriate notation in accordance with FIG. 2. It should be recalled, however, that the particular notation or descriptive nomenclature selected for use in teaching the present invention is in no way intended to limit the scope of the invention.

The initial hypothesis advanced by the invention in deriving a relationship between overall octane number and the constituents of a gasoline sample is that the coefficient by which the volume fraction of each constituent is to be multiplied is itself a function of the octane level of the total composition.

Incorporating this thesis into the prior art equation, denominated (1) above, the relationship becomes $$ON = \Sigma V_i(A_i ON + B_i) \tag{2}$$

which is summed over the range $$i = O \text{ to } n$$

where n is the total number of differentiated constituents of the sample.

For the special case where the sample contains only a single constituent i, $$ON_i = A_i ON_i + B_i \tag{3}$$

so that the second linear term may be eliminated and the above relationship substituted in equation (2) to produce the equation $$ON = \Sigma V_i[ON_i + A_i(ON - ON_i)] \tag{4}$$

where $ON_i$ is the octane number for a given component. In order to simplify the equation (4), it may be solved for the octane number ON of the overall sample to yield $$ON = \frac{\Sigma V_i(1 - A_i) ON_i}{1 - \Sigma V_i A_i} \tag{5}$$

It is now possible by using multiple regressions or a similar mathematical technique, along with prior experimental results, to derive an appropriate coefficient A for any component i. For instance, by utilizing equation (4) a standard error SE may be generated in accordance with the equation $$SE = \sum_{i=1}^{m} (ON_{obs} - \Sigma V_i[ON_i + A_i(ON^* - ON_i)])^2 \tag{6}$$

where
m is the total number of empirical observations;
$ON_{obs}$ is the observed octane number for any observation i; and
$ON^*$ is a trial octane number used for successive regressions.

In order to ascertain the constants $A_i$ which give rise to an octane number within an acceptable standard error a first standard error (SE) is calculated in accordance with equation (6), taking $ON^*$ to be equal to $ON_{obs}$. A set of values for the coefficients $A_i$ are then selected by a method such as least squares, and substituted in equation (5) to obtain a predicted octane number ON. The predicted octane number which is thus derived is then used for $ON^*$ in equation (6) and a new set of coefficients $A_i$ selected by an appropriate search method. The new coefficients $A_i$ are again substituted into equation (5) to obtain a predicted octane number which is again substituted for ON* in equation (6) to generate yet another set of coefficients $A_i$. The procedure is repeated until the n substituted coefficients $A_i$ no longer change significantly upon repeating the procedure.

It will be recognized that the actual values used for coefficients $A_i$ will depend upon a number of factors, not the least of which is the identity of each of the n components. At one extreme, the n components could comprise each and every compound contained in a gasoline sample. However, the number of compounds involved for reformate gasoline would range between 150 and 200. Such a large number of sample constituents renders the octane number correlation procedure unduly complex, and burdensome in use.

It is apparent that one of the major benefits of creating mathematical approximations or "models" of physical phenomena is the added simplicity and resulting ease in calculation which is achieved. This goal is most often met by considering only those factors which are of significance and disregarding all else. In analyzing motor fuel, however, the relative significance of the contributions of the varied compounds is not fully known or explained.

In the present instance, and in view of the great number of individual compounds which are found in a sample of reformate gasoline it has been found desirable to gather the compounds together into a relatively small number of groups, which groups can then be easily manipulated in accordance with the foregoing equations.

While there are many different characteristics which might be selected as a basis for grouping compounds together, in a presently preferred embodiment the inventor has found that by classifying the various compounds into the sixteen categories or groups set forth in Table II both highly accurate results and ease in calculation can be achieved.

After the member of each group is identified an octane number $ON_i$ is associated with each group i. The octane number $ON_i$ selected for any group corresponds to the approximate average of the octane numbers for each of the pure compounds thereof, regardless of the actual composition of the group in the particular sample under test. The octane numbers used for the pure compounds are those established by the American Society for Testing Materials (ASTM).

In Table II the octane numbers for 16 groups are set forth. The octane numbers designated $ON_i$ are for an unleaded gasoline sample, while those designated $ON_i'$ are for leaded (i.e., 3 ml.) gasoline.

TABLE II

| Pure Compounds In Group | $ON_i$ | $N_i'$ |
|---|---|---|
| n-pentane | 68.0 | 84.0 |
| iso-pentane | 92.0 | 101.5 |
| n-hexane | 24.8 | 65.3 |
| monomethyl hexane | 77.5 | 96.8 |
| doubly branched hexane | 97.3 | 112.0 |
| n-heptane | 0.0 | 43.5 |
| monomethyl heptane | 47.0 | 89.9 |
| doubly branched heptane | 94.2 | 96.6 |
| n-8+ carbon paraffins | 0.0 | 10.0 |
| iso-8-+ carbon paraffins | 40.0 | 60.0 |
| benzene | 105.0 | 109.0 |
| toluene | 119.7 | 129.0 |
| 8 carbon aromatics | 106.2 | 107.2 |
| 9 carbon aromatics | 109.1 | 111.2 |
| 10+ carbon aromatics | 110.8 | 111.0 |

TABLE II-continued

| Pure Compounds In Group | $ON_i$ | $N_i'$ |
|---|---|---|
| all naphthenes | 86.5 | 95.2 |

In a successfully tested embodiment of the present invention in which the pure compounds of a reformate sample were segregated into 16 groups as set forth in Table II, the following coefficients A were used:

TABLE III

| Pure Compounds In Group | $A_i$ (Unleaded Fuel) | $A_i'$ (Leaded Fuel) |
|---|---|---|
| n-pentane | 0 | 0 |
| iso-pentane | 0 | 0 |
| n-hexane | 0.2266604923 | −0.4435518738 |
| monomethyl hexane | 0.2444292729 | −0.6012820019 |
| doubly branched hexane | 0.6312777312 | −2.245719403 |
| n-heptane | 0.1863006828 | −0.111846948 |
| monomethyl heptane | 0.4687498083 | −1.92498522 |
| doubly branched heptane | 0.07227285881 | 2.991516647 |
| n-8+ carbon paraffins | −0.3757691833 | 0.2438739092 |
| iso-8+ carbon paraffins | 0.3810448308 | 0.419129174 |
| benzene | 0.2362039712 | 0.1515214777 |
| toluene | 0.1280680558 | 0.07885135974 |
| 8 carbon aromatics | −0.8746013666 | 0.8641859308 |
| 9 carbon aromatics | −0.611511292 | −0.1221040803 |
| 10+ carbon aromatics | −0.7259134158 | −1.275064626 |
| all naphthenes | −0.0238941258 | 0.001953752694 |

The coefficients of Table III were obtained through the use of the iterative technique explained hereinabove in conjunction with equations (5) and (6), and using empirical data from over 4000 actual test runs conducted upon the products of several reforming processes. While the particular coefficients of Table III produce good results with the enumerated compound groups, it should be recongnized that other coefficients may serve equally well for other embodiments of the invention; particularly in instances where other grouping arrangements are utilized.

Figure 2:
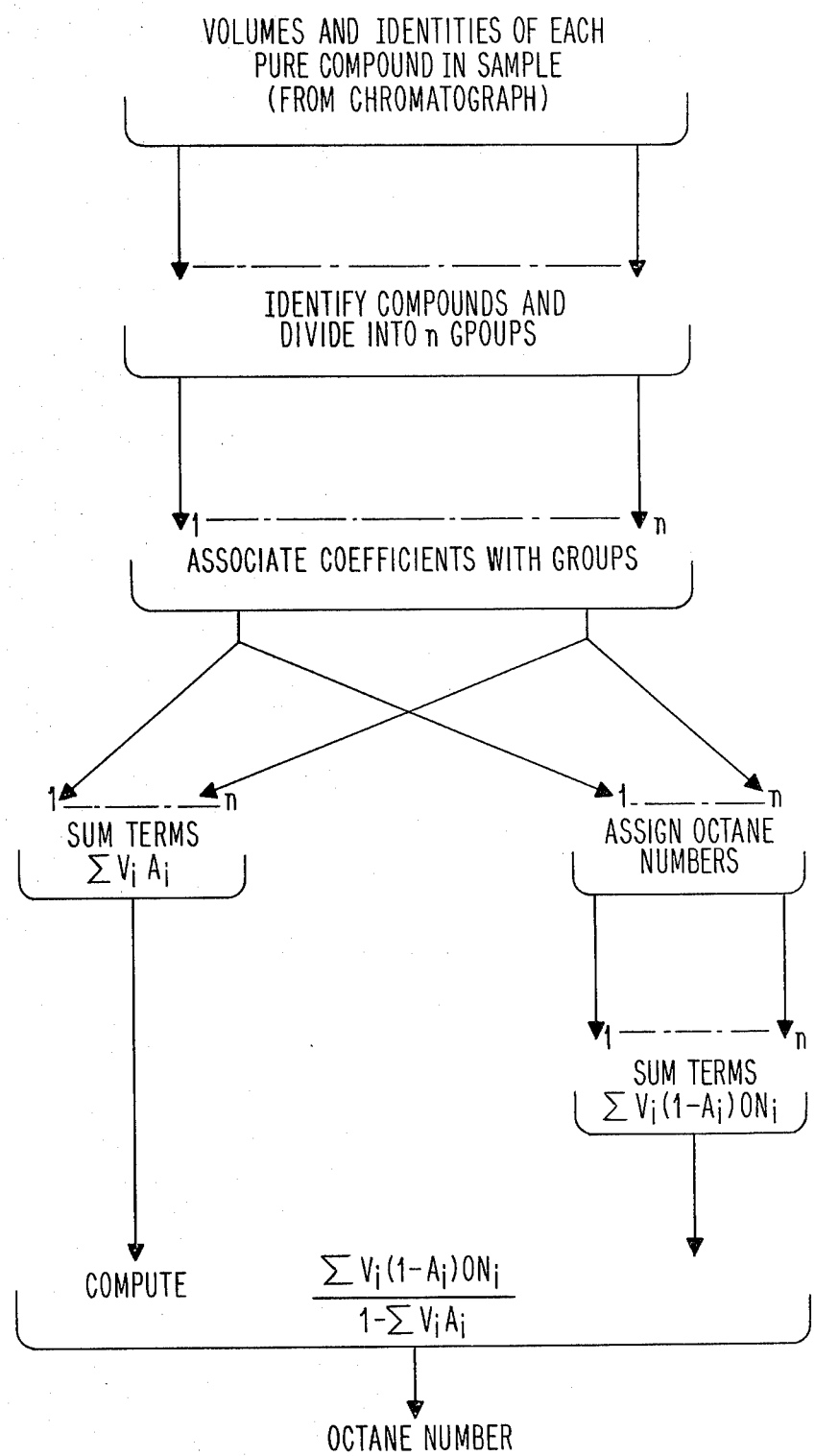
FIG. 2 is a chart indicating the flow of information, and the operations performed thereon by certain of the elements depicted in FIG. 1.

Turning now to FIG. 2 there is shown in idealized form the operation by the apparatus of FIG. 1 upon information derived from a reformate sample by means of chromatograph 32. As set forth with respect to FIG. 1, the identity and percent volume of each compound in a sample taken from the reformate stream is analyzed, and a signal bearing this information is transmitted from the appropriate transducer to computer 64. An input stage within the computer receives the information, and by determining the relative timing of a given signal, its value and the particular chromatograph column from which it is derived, the identity and relative volume of each of the compounds is determined. The various compounds are then associated into n groups, which may for instance be the groups set forth in Table II. Each of the coefficients $A_i$ are then associated with the appropriate ones of the n groups, and the product of the relative volume of each group and its coefficient is derived. The sum of the n products is then subtracted from unity to form the denominator of the expression comprising the right-hand side of equation (6).

At the same time appropriate octane numbers, which may in the present example be those listed in Table II, are assigned to each of the n groups. Means within computer 64 then derive the difference between the coefficient $A_i$ for each group and unity. This difference is then multiplied by the relative volume $V_i$ and octane number $ON_i$ for the group in accordance with the expression $V_i(1-A_i)ON_i$. Computer 64 then sums the n expressions to obtain the numerator of the right-hand term of equation (6).

It will now be understood that the resulting fraction $$\frac{\sum_{i=1}^{n} V_i(1 - A_i) ON_i}{1 - \sum_{i=1}^{n} V_i A_i}$$

may be solved in a straightforward manner to yield a predicted or estimated octane number for the sample under test.

In view of the foregoing discussion, persons skilled in the art will now recognize that the described approach may readily be implemented by programming a general purpose digital computer using standard techniques. One successfully tested embodiment of the invention utilized a digital computer manufactured by the International Business Machines Corporation which had been programmed by the manufacturer's representatives in a program language designated APL. As is now well known, APL is an exceedingly powerful language which enables data to be easily manipulated in matrix form, and has the further advantage of responding to simplified instructional programs. For instance, the program used to cause such a computer system to derive the octane number represented in equation (5) is simply $$ON \leftarrow (V + \cdot \times A \times 1 - B) \div 1 - V + \cdot \times B$$

wherein the symbol A designates the matrix of octane number values given in Table II and B represents the matrix of predetermined coefficients set forth in Table III (respectively designated $ON_i$ and $A_i$ in equation (5)).

Investigation has shown that octane numbers predicted in the foregoing manner by the apparatus set forth hereinabove exhibit a repeatability characteristic which is very similar to octane numbers obtained from tests on knock engines. In particular, the repeatability of test results with knock engines is known to be best for motor fuels exhibiting an octane rating in the neighborhood of 90. The ability to obtain identical results for subsequent tests diminishes as the octane rating of the fuel varies from 90 in either an increasing or a decreasing manner. This characteristic is also exhibited by the system of the present invention in that test results become more repeatable as octane numbers approach 90 from either direction. In this manner, although the apparent error would seem to increase for octane numbers substantially lesser than or in excess of 90, in fact the predicted numbers correlate extremely well with those which would be obtained from tests on the same fuel, conducted on a knock engine.

The degree of accuracy achieved with the system of this invention is adequate for control of refinery equipment for preparing gasoline components and for blending components to prepare a finished motor fuel, since control responsive to octane number has been heretofore practiced on the basis of engine test results of substantially equivalent accuracy. The system is applicable to components or motor fuel containing liquid hydrocarbons boiling up to the desired end boiling point, variously from about 375° F. to 435° F.

The degree of accuracy in the system may, of course, be enhanced by associating the individual compounds with a greater number of groups. The ideal level of accuracy would be attained by considering each compound separately, apart from all others. This entails development of coefficients such as those in Table III for each of the enormous number of compounds and applying these in the computer program. There are about 20 octane isomers and the number of isomers rises steeply with increasing number of carbon atoms. Attention is again directed to the difference in number of necessary groups for acceptable accuracy with respect to six and seven carbon atom compounds as compared with higher paraffins.

It will be immediately apparent that the monitor and control technique here described may be applied to examination of a naphtha charge and feed-forward control of, e.g. reforming or Selectoforming.

As will be evident from the foregoing description, certain aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the invention.

I claim:

1. Apparatus for automatically determining the octane number of a gasoline or a gasoline component constituted by a complex mixture of individual hydrocarbon compounds boiling in the gasoline range, comprising:
    means for separating a sample of said gasoline into the pure compounds present in said sample;
    means for measuring the quantity of each of said pure compounds;
    means responsive to the output of said measuring means for grouping said compounds into groups including at least:
        (a) n-hexane,
        (b) hexanes having a single carbon atom in branched chain position,
        (c) hexanes having two carbon atoms in branched chain position,
        (d) n-heptane,
        (e) heptanes having a single carbon in branched chain position, and
        (f) heptanes having two carbon atoms in branched chain position;
    means for adding the individual quantities in each group to determine the quantity in said sample of all compounds in each group;
    means for multiplying each of the group quantities determined in said adding step by a coefficient characteristic of octane number contribution by said group to provide values representative of octane number for the said groups; and
    means for summing said last named values to derive the octane number of said sample.

2. Apparatus according to claim 1, wherein said measuring means is a chromatograph producing an output which resolves the peaks for each of the individual pure compounds of the gasoline or gasoline component supplied to the chromatograph; and
    means for converting the output of said chromatograph into digital signals representing the amount of each pure component in said gasoline or gasoline sample.

3. A processing system including reforming apparatus for converting a hydrocarbon stream into a gasoline or a gasoline component constituted by a complex mixture of individual hydrocarbon compounds boiling in the gasoline range, comprising:

measuring apparatus coupled to said reforming apparatus for producing an output representing the quantity of each pure compound present in said gasoline or gasoline component;

means coupled to said measuring apparatus for associating the said quantities of individual compounds in groups and adding the individual quantities in each group to determine the quantity in said sample of all compounds in each group, said groups including as separate entities at least:
(a) n-hexane,
(b) hexanes having a single carbon atom in branched chain position,
(c) hexanes having two carbon atoms in branched chain position,
(d) n-heptane,
(e) heptanes having a single carbon in branched chain position, and
(f) heptanes having two carbon atoms in branched chain position;

means for multiplying each of the group quantities determined in said adding step by a coefficient characteristic of octane number contribution by said group to provide values representative of octane number for the said groups and summing said last named values to produce an octane number signal; and means responsive to said octane number signal for controlling said reforming apparatus to produce a product having a desired octane number.

* * * * *

UNITED STATES PATENT AND TRADEMARK OFFICE
CERTIFICATE OF CORRECTION

PATENT NO. : 4,251,870
DATED : February 17, 1981
INVENTOR(S) : Stephen B. Jaffe

It is certified that error appears in the above-identified patent and that said Letters Patent are hereby corrected as shown below:

Column 10, line 24, "0.8641859308" should be -- -0.8641859308--

Column 11, line 31, "ON⇐(V+·xAx1-B) ÷ 1-V+·xB" should be

--ON⇐(V+·x$\underline{A}$x1-$\underline{B}$) ÷ 1-V+·x$\underline{B}$--

Signed and Sealed this

Twenty-sixth Day of May 1981

[SEAL]

Attest:

RENE D. TEGTMEYER

Attesting Officer     Acting Commissioner of Patents and Trademarks